US012693215B2

(12) United States Patent (10) Patent No.: US 12,693,215 B2
Araya (45) Date of Patent: Jul. 28, 2026

(54) GAS MEASUREMENT APPARATUS

(71) Applicant: SHIMADZU CORPORATION, Kyoto (JP)

(72) Inventor: Katsuhiko Araya, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 315 days.

(21) Appl. No.: 18/575,608

(22) PCT Filed: Jul. 6, 2022

(86) PCT No.: PCT/JP2022/026807
§ 371 (c)(1),
(2) Date: Jun. 12, 2024

(87) PCT Pub. No.: WO2023/282282
PCT Pub. Date: Jan. 12, 2023

(65) Prior Publication Data
US 2024/0377318 A1 Nov. 14, 2024

(30) Foreign Application Priority Data
Jul. 9, 2021 (JP) ................................. 2021-114191

(51) Int. Cl.
*G01N 21/3504* (2014.01)
*G01N 1/22* (2006.01)
*G01N 33/00* (2006.01)
(52) U.S. Cl.
CPC ....... *G01N 21/3504* (2013.01); *G01N 1/2247* (2013.01); *G01N 33/0037* (2013.01); *G01N 33/004* (2013.01); *G01N 33/0042* (2013.01)
(58) Field of Classification Search
CPC ............. G01N 21/3504; G01N 1/2247; G01N 33/0037; G01N 33/004; G01N 33/0042
See application file for complete search history.

(56) References Cited

U.S. PATENT DOCUMENTS 5,572,032 A 11/1996 Fujiwara et al.
2015/0136616 A1* 5/2015 Friedrich ........... G01N 33/0059
205/785.5

FOREIGN PATENT DOCUMENTS

EP 2500711 A2 9/2012
JP 50-059090 A 5/1975
(Continued)

OTHER PUBLICATIONS

EESR dated May 26, 2025 for corresponding application No. EP 22837696.8.

(Continued)

*Primary Examiner* — Jamil Ahmed
(74) *Attorney, Agent, or Firm* — Muir Patent Law, PLLC

(57) ABSTRACT

A gas measurement apparatus includes a sample gas line that dehumidifies sample gas, a reference gas line that generates reference gas dehumidified after a gas component to be analyzed is removed from sample gas, a first switch that selectively supplies gas that has passed through the reference gas line and gas that has passed through the sample gas line to a sample cell, a light source that irradiates the sample cell with light, and a detection unit that detects intensity of light that has passed through the sample cell after being emitted from the light source to the sample cell. The gas component to be analyzed includes $SO_2$ gas. The reference gas line includes a bubbling separator that bubbles sample gas with water to remove $SO_2$ gas from sample gas and a dehumidification apparatus that dehumidifies gas that has passed through the bubbling separator.

10 Claims, 6 Drawing Sheets

(56) References Cited

FOREIGN PATENT DOCUMENTS

| JP | 52-123978 | A | | 10/1977 | | |
|----|-----------|---|---|---------|---|---|
| JP | S56025250 | U | | 3/1981 | | |
| JP | S59-029748 | U | | 2/1984 | | |
| JP | H09-049797 | A | | 2/1997 | | |
| JP | H0949797 | A | * | 2/1997 | ............ | G01N 21/35 |
| JP | 10-165758 | A | | 6/1998 | | |
| JP | 2004-061207 | A | | 2/2004 | | |
| JP | 2005010007 | A | * | 1/2005 | ............ | G01N 21/35 |
| JP | 2012-189549 | A | | 10/2012 | | |

OTHER PUBLICATIONS

Trieu Vuong Dinh et al., "A review on non dispersive infrared gas sensors: Improvement of sensor detection limit and interference correction", Sensors and Actuators B: Chemical, Mar. 14, 2016, pp. 529 538, vol. 231, Elsevier.
PCT Written Opinion of the International Searching Authority of PCT/JP2022/026807 dated Sep. 20, 2022.

* cited by examiner

GAS MEASUREMENT APPARATUS

TECHNICAL FIELD

The present disclosure relates to a gas measurement apparatus.

BACKGROUND ART

Japanese Patent Laying-Open No. 9-49797 (PTL 1) discloses an infrared gas analyzer that measures a concentration of a gas component while switching between sample gas and reference gas is made. In this infrared gas analyzer, a three-way valve is switched to alternately supply sample gas and reference gas into a cell in prescribed cycles. Concurrently, a motor rotates a sector so that infrared light from a light source is intermittently emitted to the inside of the cell. A detector thus alternately detects infrared light that has passed through sample gas or reference gas to allow analysis of a gas component based on a ratio between a reference gas detection output and a sample gas detection output. Japanese Utility Model Laying-Open No. 59-29748 (PTL 2) discloses a dual-beam gas analyzer including two cells.

CITATION LIST

Patent Literature

PTL 1: Japanese Patent Laying-Open No. 9-49797
PTL 2: Japanese Utility Model Laying-Open No. 59-29748

SUMMARY OF INVENTION

Technical Problem

In the infrared gas analyzer, when a gas component (which is referred to as an interference component below) having an infrared ray absorption band which overlaps with that of a gas component to be measured is contained in sample gas, a measurement error is caused. For example, in measurement of sulfur dioxide ($SO_2$) in combustion exhaust gas, HC and $CO_2$ are present as interference components in combustion exhaust gas.

In the infrared gas analyzer disclosed in Japanese Patent Laying-Open No. 9-49797 (PTL 1), the atmosphere not containing $SO_2$ which is a gas component to be measured can be employed as reference gas. The atmosphere, however, contains substantially no HC and $CO_2$ which are interference components in measurement of $SO_2$, although this literature is silent about this fact. Therefore, in output of a difference in infrared absorption between sample gas and reference gas, a measurement error may be caused under the influence by the interference components.

In contrast, there is also a method of separately and successively measuring a concentration of an interference component and correcting in real time an error caused by the influence by the interference component based on a result of measurement. This method, however, can be used only when a type of the interference component in sample gas and an approximate concentration thereof are known in advance, and in addition, a feature that concurrently detects the concentration of the interference component is required, which results in high cost.

Furthermore, a method of addressing interference by providing in an optical path, an optical filter including a multilayer film for narrowing a transparent wavelength band or a cell filled with interference gas at a high concentration is also available. Though this method is effective to lessen interference to some extent, the effect is often insufficient and some interference error remains. In addition, introduction of such an optical filter in the optical path leads to attenuation of light and hence poorer accuracy in measurement.

An object of the present disclosure is to provide a gas measurement apparatus that can achieve improvement in accuracy in detection of $SO_2$ while development cost therefor is suppressed.

Solution to Problem

The present disclosure relates to a gas measurement apparatus that measures a gas component to be analyzed in sample gas. The gas measurement apparatus includes a sample gas line that dehumidifies the sample gas, a reference gas line that generates reference gas dehumidified after the gas component to be analyzed is removed from the sample gas, a sample cell, a first switch that selectively supplies to the sample cell, gas that has passed through the reference gas line and gas that has passed through the sample gas line, a light source that irradiates the sample cell with light, and a detection unit that detects intensity of light that has passed through the sample cell after being emitted from the light source to the sample cell. The gas component to be analyzed includes $SO_2$ gas. The reference gas line includes a bubbling separator that bubbles the sample gas with water to remove $SO_2$ gas from the sample gas and a dehumidification apparatus that dehumidifies gas that has passed through the bubbling separator.

Advantageous Effects of Invention

The gas measurement apparatus in the present disclosure removes gas to be analyzed from sample gas with the use of the bubbling separator to obtain reference gas when gas to be analyzed is water-soluble and interference component gas is water-insoluble. Therefore, since interference component gas at the same concentration is present also in reference gas, influence by interference component gas can be canceled.

DESCRIPTION OF EMBODIMENTS

Figure 1:
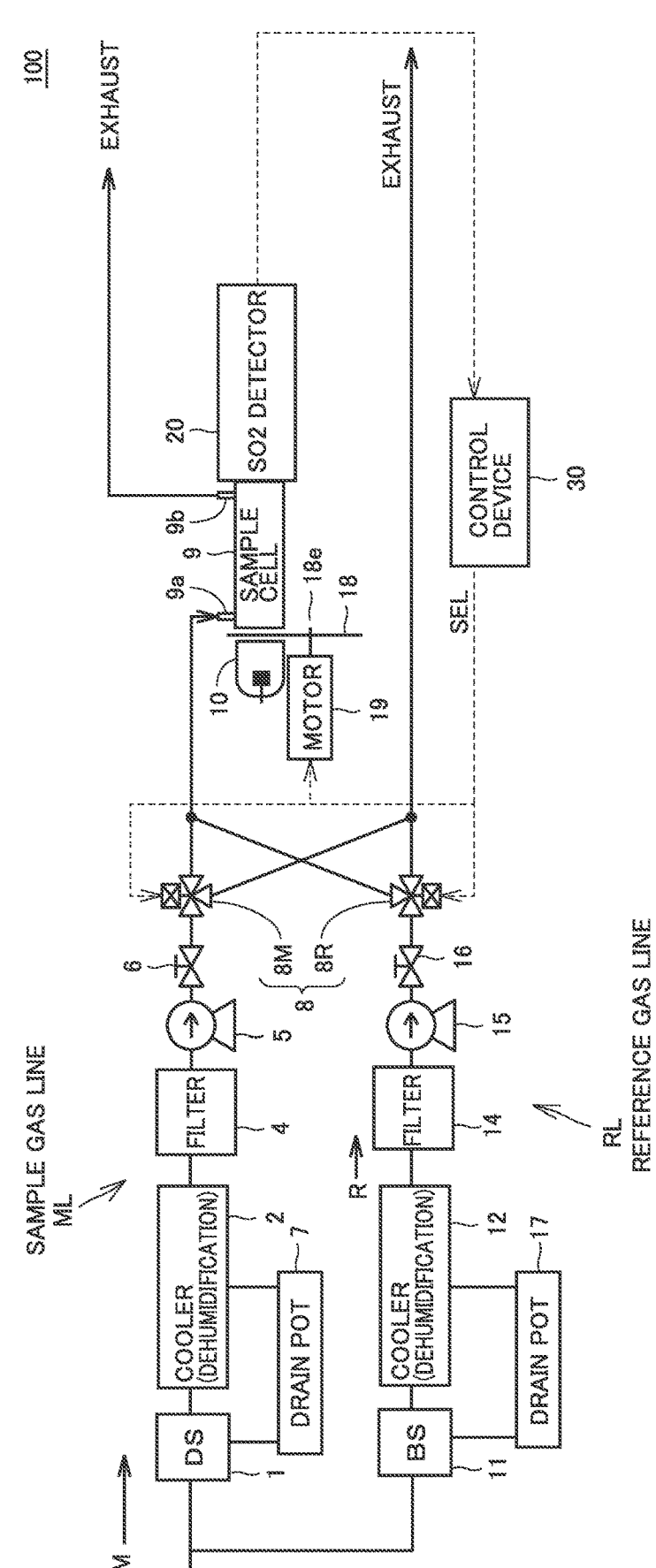
FIG. 1 is a diagram schematically showing a configuration of a gas measurement apparatus in a first embodiment.

An embodiment of the present invention will be described in detail below with reference to the drawings. The same or corresponding elements in the drawings have the same reference characters allotted and description thereof will not be repeated.

First Embodiment

Figure 2:
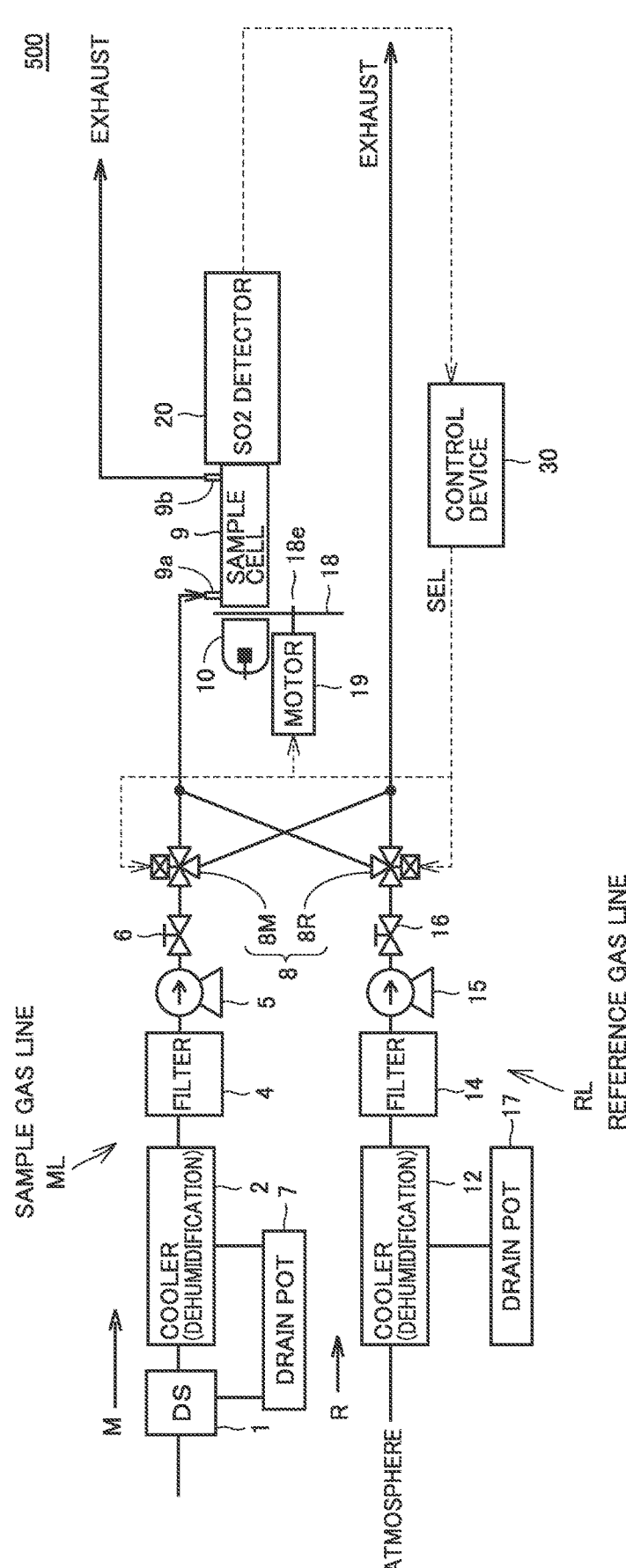
FIG. 2 is a diagram schematically showing a configuration of a gas measurement apparatus in a study example.

FIG. 1 is a diagram schematically showing a configuration of a gas measurement apparatus in a first embodiment. FIG. 2 is a diagram schematically showing a configuration of a gas measurement apparatus in a study example. A gas measurement apparatus 100 in FIG. 1 is different from a gas measurement apparatus 500 in FIG. 2 in configuration of a reference gas line RL. The configuration in FIG. 1 will be described below in comparison to FIG. 2.

Gas measurement apparatus 100 shown in FIG. 1 includes a sample gas line ML, reference gas line RL, a switch 8, and a sample cell 9.

Sample gas M is introduced into sample gas line ML. Sample gas line ML includes a drain separator 1 that separates drainage water produced by natural cooling, a cooler 2 that dehumidifies sample gas by cooling the same, and a drain pot 7 where drainage water separated in drain separator 1 and cooler 2 is accommodated.

Sample gas line ML further includes a filter 4 through which sample gas M passes, a pump 5 that delivers sample gas M, and a needle valve 6 that regulates a flow rate of sample gas M.

Sample gas line ML above is the same in configuration between the study example in FIG. 2 and the first embodiment in FIG. 1.

In the study example in FIG. 2, the atmosphere is introduced into reference gas line RL. In the first embodiment, on the other hand, sample gas M is introduced also into reference gas line RL. Reference gas line RL shown in FIG. 1 includes a bubbling separator 11 that bubbles sample gas M with drainage water produced by natural cooling, a cooler 12 that dehumidifies sample gas (reference gas R) that has passed through bubbling separator 11 by cooling the same, and a drain pot 17 where drainage water separated in bubbling separator 11 and cooler 12 is accommodated. Bubbling separator 11 removes a water-soluble gas component in sample gas M.

Reference gas line RL further includes a filter 14 through which reference gas R passes, a pump 15 that delivers reference gas R, and a needle valve 16 that regulates a flow rate of reference gas R.

As set forth above, in the present embodiment, gas obtained by bubbling of sample gas M with water to remove water-soluble $SO_2$ is used as reference gas R. Bubbling separator 11 or the like is used for bubbling with water. In an example where combustion exhaust gas in a factory, an incinerator plant, or the like is adopted as sample gas M, bubbling with water can be performed with the use of moisture in sample gas M itself, and hence bubbling separator 11 does not have to separately be supplied with water. Bubbling separator 11 may be replenished with water and may be replenished with drainage water from cooler 2 or 12.

Switch 8 and sample cell 9 which will be described below are common between FIGS. 1 and 2.

Switch 8 includes a three-way valve 8M arranged in sample gas line ML and a three-way valve 8R arranged in reference gas line RL. Three-way valve 8M or 8R defines a flow channel based on a selection signal SEL such that gas that has passed through one of reference gas line RL and sample gas line ML is sent to sample cell 9 and gas that has passed through the other thereof is exhausted.

Gas measurement apparatus 100 further includes a motor 19, a sector 18, a light source 10, an $SO_2$ detector 20, and a control device 30.

Sample cell 9 includes a gas inlet 9a and a gas outlet 9b. Sample gas M or reference gas R is supplied through switch 8 from gas inlet 9a into sample cell 9 and discharged from gas outlet 9b. Light source 10 that emits infrared light is disposed at one end of sample cell 9 and $SO_2$ detector 20 that detects infrared light that has passed through sample cell 9 is disposed at the other end of sample cell 9.

Sector 18 that allows or prevents irradiation with infrared light is provided between light source 10 and the end of sample cell 9. This sector 18 includes a light cut-off portion and a light transmission portion. Sector 18 is configured to rotate around a sector rotation axis 18e. When the light transmission portion is located over sample cell 9, the inside of sample cell 9 is irradiated with infrared light, and when the light cut-off portion is located over sample cell 9, irradiation of the inside of sample cell 9 with infrared light is cut off. Control device 30 controls a rotational position of sector 18 by means of motor 19 and controls drive of switch 8 with selection signal SEL.

$SO_2$ absorbs light ($SO_2$: 7.4 μm) at a specific wavelength in an infrared range. Therefore, $SO_2$ detector 20 which is sensitive only to this wavelength can measure a concentration of $SO_2$ by measuring infrared absorption subsequently to passage through measurement gas.

Gas to be detected in sample gas is sealed in $SO_2$ detector 20, and $SO_2$ detector 20 detects intensity of infrared light at a frequency specific to gas to be detected, based on variation in pressure therein. Control device 30 that receives a detection output from $SO_2$ detector 20 performs prescribed signal processing to calculate a concentration value indicating the concentration of measurement gas in sample gas.

In a configuration as in gas measurement apparatus 500 in the comparative example shown in FIG. 2, reference gas R does not contain HC and $CO_2$ which are interference components but sample gas M contains the interference components. An absorption wavelength band of 7.2 μm of a C—H bond of HC is close to an absorption wavelength band of 7.4 μm of $SO_2$. Therefore, an error is caused in measurement of the concentration of $SO_2$ under the influence by HC. An absorption wavelength band of 4.3 μm of $CO_2$, on the other hand, is distant from the absorption wavelength band of 7.4 μm of $SO_2$. The concentration of $CO_2$ in sample gas, however, is generally significantly higher than the concentration of $SO_2$. Therefore, even slight overlapping of the absorption wavelength band leads to influence by the interference component and the error is caused in measurement of the concentration of $SO_2$.

In contrast, according to gas measurement apparatus 100 in the first embodiment shown in FIG. 1, the interference components such as HC and $CO_2$ low in solubility in water are not substantially removed by bubbling with water but are contained in reference gas R. Therefore, in a difference in infrared ray absorption between sample gas M and reference gas R, influence by the interference component is canceled. Therefore, the concentration of $SO_2$ can be measured without being affected by the interference component. According to the first embodiment, even when the interference component or the concentration thereof is unknown, influence by the interference component can be removed more inexpensively and more accurately than in a conventional technique.

Modification of First Embodiment

Though the first embodiment illustrates the gas measurement apparatus configured to alternately introduce sample gas and reference gas into the sample cell, a similar reference gas line may be applied to a gas measurement apparatus including two cells of a sample cell and a reference cell.

Figure 3:
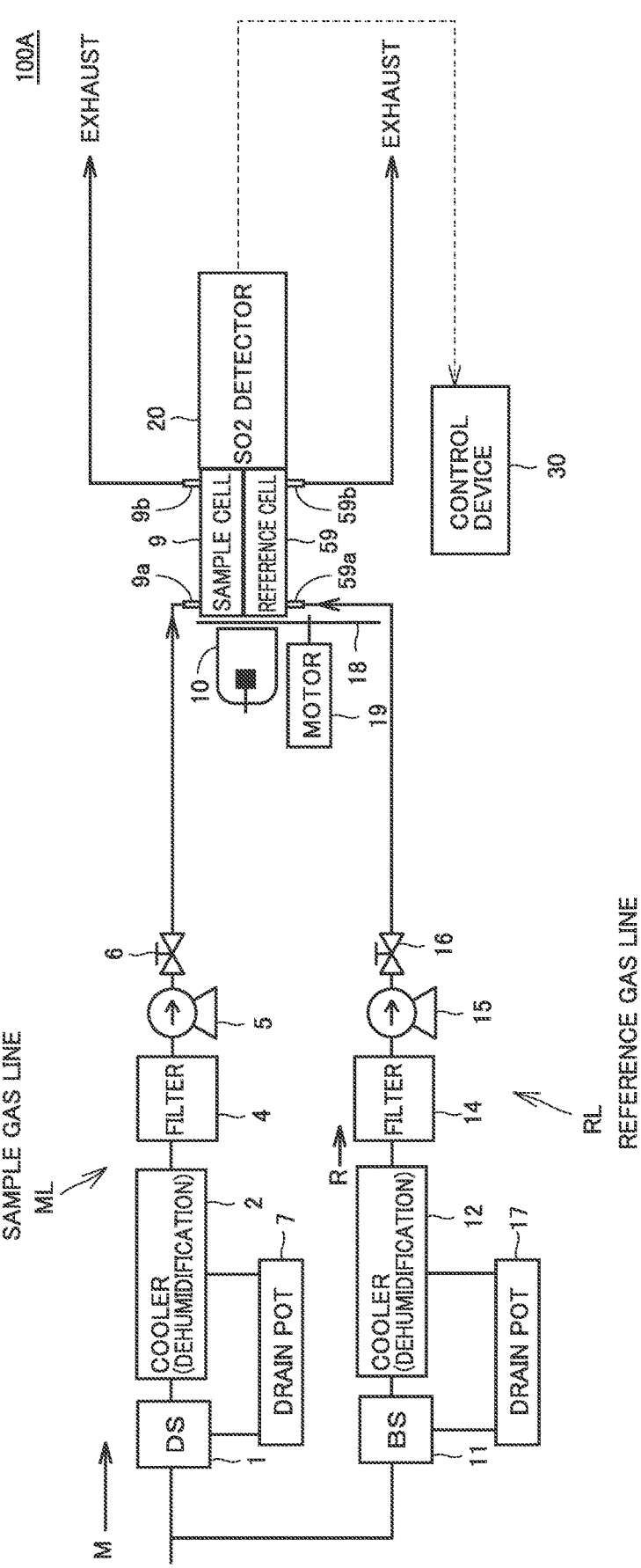
FIG. 3 is a diagram schematically showing a configuration of a gas measurement apparatus in a modification of the first embodiment.

FIG. 3 is a diagram schematically showing a configuration of a gas measurement apparatus in a modification of the first embodiment. A gas measurement apparatus 100A shown in FIG. 3 includes a reference cell 59 instead of switch 8 in the configuration of gas measurement apparatus 100 shown in FIG. 1. Since gas measurement apparatus 100A is otherwise similar in configuration to gas measurement apparatus 100 shown in FIG. 1, description will not be repeated.

Sample gas that has passed through sample gas line ML is introduced as it is into sample cell 9. Reference cell 59 includes a gas inlet 59a and a gas outlet 59b. Reference gas that has passed through reference gas line RL is introduced from gas inlet 59a of reference cell 59 into reference cell 59 and thereafter discharged from gas outlet 59b. SO₂ detector 20 detects a difference between intensity of infrared light that has been transmitted through sample cell 9 and intensity of infrared light that has passed through reference cell 59.

The gas measurement apparatus including the two cells of the sample cell and the reference cell can thus also similarly eliminate influence by the interference component.

Second Embodiment

The first embodiment illustrates an SO₂ measurement apparatus in which sample gas, from which SO₂ is removed by dissolution by bubbling with water, is employed as reference gas in an infrared gas analyzer for measurement with switching between sample gas and reference gas being made. There is a demand, however, for a multiple-component measurement apparatus as a gas measurement apparatus capable of simultaneously measuring a component other than SO₂.

In an example of simultaneous measurement of NOx (=NO+NO₂), CO, and CO₂ other than SO₂ with a single measurement apparatus, in a method of generating reference gas according to the first embodiment, NO, CO, and CO₂ low in water solubility are not removed by the bubbling separator, and gas containing them is inappropriate as reference gas for measurement of NOx, CO, and CO₂.

In particular, it is difficult to remove NO and CO₂ continuously in a stable manner to a level allowable for reference gas (that is, a ratio of removal not lower than 99.9% to the atmospheric concentration). Therefore, it is difficult to implement a multiple-component gas measurement apparatus with the configuration in the first embodiment as it is. CO may be removed by oxidation thereof to CO₂ by an oxidation catalyst. Catalyst poisoning, however, gives rise to a problem in maintenance of necessary oxidation efficiency in a stable manner for a long time.

Therefore, for measurement of multiple components with the use of the gas measurement apparatus in the first embodiment that achieves lessening of influence by interference, a consecutive measurement apparatus that consecutively measures NOx, CO, and CO₂ should separately be provided, which gives rise to a problem of increase in cost and a large footprint of the measurement apparatus or poor efficiency in installation.

In a second embodiment, a three-way valve 13 is provided downstream from bubbling separator 11 so that gas (R1) resulting from passage of sample gas through bubbling separator 11 and the atmosphere (R2) are alternately used as reference gas while switching between gas and the atmosphere is made.

Figure 4:
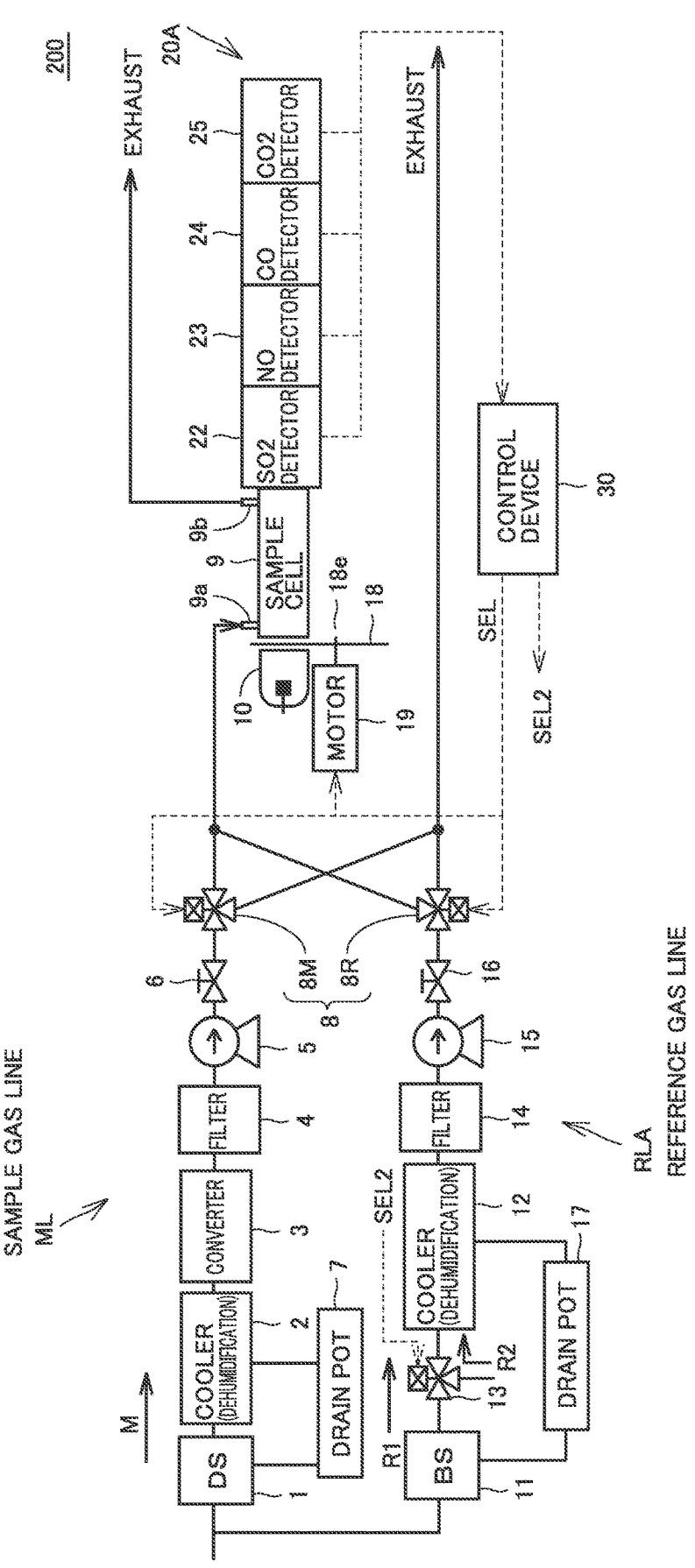
FIG. 4 is a diagram schematically showing an overall configuration of a gas measurement apparatus in a second embodiment.

FIG. 4 is a diagram schematically showing an overall configuration of a gas measurement apparatus in the second embodiment.

A gas measurement apparatus 200 shown in FIG. 4 includes a reference gas line RLA instead of reference gas line RL and includes a detection unit 20A instead of SO₂ detector 20 in the configuration of gas measurement apparatus 100 shown in FIG. 1. Since gas measurement apparatus 200 is common to gas measurement apparatus 100 in sample gas line ML, switch 8, sample cell 9, motor 19, sector 18, and light source 10, description thereof will not be repeated.

Reference gas line RLA shown in FIG. 4 is different from reference gas line RL shown in FIG. 1 in that three-way valve 13 is added between bubbling separator 11 and cooler 12. Three-way valve 13 selects one of reference gas R1 that has passed through bubbling separator 11 and reference gas R2 which is the atmosphere in response to a selection signal SEL2 provided by control device 30, so that selected gas is sent to cooler 12. Since bubbling separator 11, cooler 12, drain pot 17, filter 14, pump 15, and needle valve 16 are the same as in FIG. 1, description thereof will not be repeated.

Detector 20A includes an SO₂ detector 22, an NO detector 23, a CO detector 24, and a CO₂ detector 25 that detect SO₂, NO, CO, and CO₂, respectively.

SO₂, NO, CO, and CO₂ absorb light at respective specific wavelengths in the infrared range (SO₂: 7.4 μm, NO: 5.3 μm, CO: 4.6 μm, and CO₂: 4.3 μm). Therefore, the concentration of each component can be measured by measurement of infrared absorption subsequently to passage through measurement gas with the detector that is sensitive only to each of these wavelengths.

Gas to be detected in sample gas is sealed in each detector, and the detector detects intensity of infrared light at a frequency specific to gas to be detected, based on variation in pressure therein. Control device 30 that receives a detection output from detection unit 20A then performs prescribed signal processing to calculate a concentration value indicating the concentration of measurement gas in sample gas.

Figure 5:
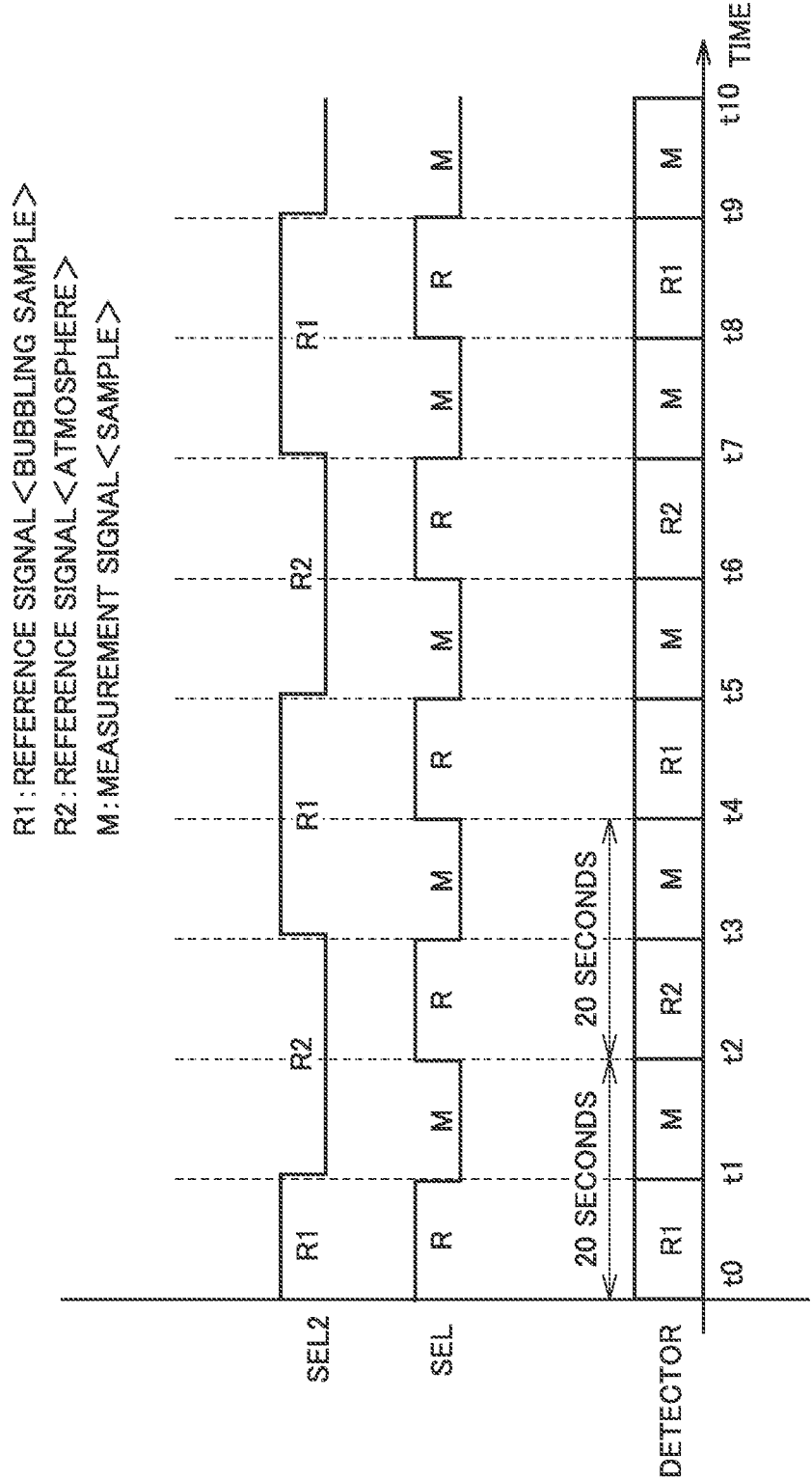
FIG. 5 is a diagram for illustrating reading of a signal by a detector.

FIG. 5 is a diagram for illustrating reading of a signal by the detector. Switch 8 receives input of selection signal SEL and three-way valve 13 receives input of selection signal SEL2.

In an example, switching between reference gas R1 and reference gas R2 is made every twenty seconds in response to selection signal SEL2 as in FIG. 5. Switching between sample gas M and reference gas R is made every ten seconds in response to selection signal SEL.

A detection signal of reference gas R1 and a detection signal of reference gas R2 are alternately read, with a detection signal of sample gas M being interposed. During periods between time t0 and time t2, between time t4 and time t6, between time t8 and time t10, . . . , control device 30 measures the SO₂ concentration based on a difference between the detection signal of reference gas R1 in a first half and the detection signal of sample gas M in a latter half detected by SO₂ detector 22.

During the periods between time t2 and time t4, between time t6 and time t8, . . . , NO, CO, and CO₂ are measured. In the first half of each period, each of NO detector 23, CO detector 24, and CO₂ detector 25 outputs the detection signal of reference gas R2 to control device 30, and in the latter half of each period, each of NO detector 23, CO detector 24, and CO₂ detector 25 outputs the detection signal of sample gas M to control device 30. Control device 30 measures the NO concentration, the CO concentration, and the CO₂ concentration based on the difference between the signal in the first half and the signal in the latter half.

Though an example in which measurement of the $SO_2$ concentration and measurement of NO, CO, and $CO_2$ are alternately conducted is illustrated in the description above, each of the detection signal of reference gas R1 and the detection signal of reference gas R2 may be stored until next measurement timing, and by simultaneous use of latest reference gas R1 and latest reference gas R2 that are stored, measurement of all components in sample gas M can also be conducted every cycle.

The configuration in the first embodiment as it is cannot implement a highly accurate multi-component analyzer. In the second embodiment, however, a single measurement apparatus can measure multiple components while an interference removal technique in measurement of the $SO_2$ concentration is used. Therefore, a multi-component analyzer including a low-interference $SO_2$ analyzer low in cost and small in footprint can be obtained.

First Modification of Second Embodiment

In FIG. 4, water-soluble $NO_2$ is converted to NO in converter 3 in sample gas line ML. Water-soluble $NO_2$ in reference gas R1, on the other hand, is removed by dissolution in bubbling separator 11 in reference gas line RLA.

Therefore, it is shown in the detection signal (which is referred to as a first signal) of reference gas R1 obtained from NO detector 23 during a period from time t0 to time t1 in FIG. 5 that the NO concentration corresponding to water-soluble $NO_2$ is lower than in the detection signal (which is referred to as a second signal) of sample gas M obtained from NO detector 23 during a period from time t1 to time t2.

Therefore, control device 30 can secondarily measure the $NO_2$ concentration based on the difference between the second signal and the first signal obtained from NO detector 23. With the use of this feature, a multiple-component gas measurement apparatus capable of measuring the $NO_2$ concentration can also be obtained.

Second Modification of Second Embodiment

Though the second embodiment illustrates the gas measurement apparatus configured to alternately introduce sample gas and reference gas into the sample cell, a similar reference gas line may be applied to a gas measurement apparatus including two cells of a sample cell and a reference cell.

Figure 6:
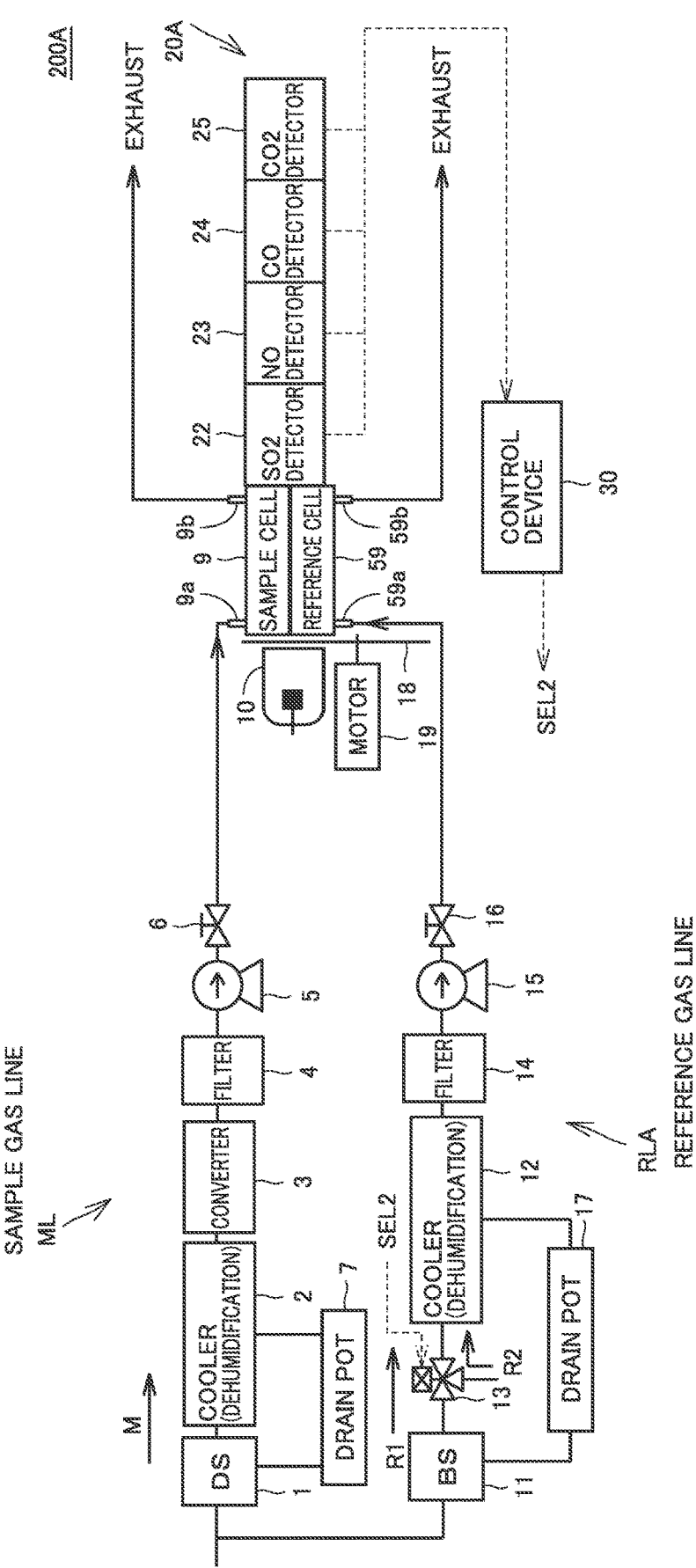
FIG. 6 is a diagram schematically showing a configuration of a gas measurement apparatus in a modification of the second embodiment.

FIG. 6 is a diagram schematically showing a configuration of a gas measurement apparatus in a modification of the second embodiment. A gas measurement apparatus 200A shown in FIG. 6 includes reference cell 59 instead of switch 8 in the configuration of gas measurement apparatus 200 shown in FIG. 4. Since gas measurement apparatus 200A is otherwise similar in configuration to gas measurement apparatus 200 shown in FIG. 4, description will not be repeated.

Sample gas that has passed through sample gas line ML is introduced as it is into sample cell 9. Reference cell 59 includes gas inlet 59a and gas outlet 59b. Reference gas that has passed through reference gas line RLA is introduced from gas inlet 59a of reference cell 59 into reference cell 59 and thereafter discharged from gas outlet 59b. SO2 detector 20 detects a difference between intensity of infrared light that has been transmitted through sample cell 9 and intensity of infrared light that has passed through reference cell 59.

The gas measurement apparatus including the two cells of the sample cell and the reference cell can thus also measure multiple components by a single measurement apparatus while the interference removal technique in measurement of the $SO_2$ concentration is similarly used.

Aspects

Illustrative embodiments described above are understood by a person skilled in the art as specific examples of aspects below.

(Clause 1) The present disclosure relates to a gas measurement apparatus that measures a gas component to be analyzed in sample gas. The gas measurement apparatus includes a sample gas line that dehumidifies the sample gas, a reference gas line that generates reference gas dehumidified after the gas component to be analyzed is removed from the sample gas, a sample cell, a sample gas switch that selectively supplies to the sample cell, gas that has passed through the reference gas line and gas that has passed through the sample gas line, a light source that irradiates the sample cell with light, and a detection unit that detects intensity of light that has passed through the sample cell after being emitted from the light source to the sample cell. The gas component to be analyzed includes $SO_2$ gas. The reference gas line includes a bubbling separator that bubbles the sample gas with water to remove $SO_2$ gas from the sample gas and a dehumidification apparatus that dehumidifies gas that has passed through the bubbling separator.

(Clause 2) Another embodiment of the present disclosure relates to a gas measurement apparatus that measures a gas component to be analyzed in sample gas.

The gas measurement apparatus includes a sample gas line that dehumidifies the sample gas, a reference gas line that generates reference gas dehumidified after the gas component to be analyzed is removed from the sample gas, a sample cell into which gas that has passed through the sample gas line is introduced, a reference cell into which gas that has passed through the reference gas line is introduced, a light source that irradiates the sample cell and the reference cell with light, and a detection unit that detects intensity of light that has passed through the sample cell after being emitted from the light source to the sample cell, and intensity of light that has passed through the reference cell after being emitted from the light source to the reference cell. The gas component to be analyzed includes $SO_2$ gas. The reference gas line includes a bubbling separator that bubbles the sample gas with water to remove $SO_2$ gas from the sample gas and a dehumidification apparatus that dehumidifies gas that has passed through the bubbling separator.

According to the configuration, when a gas component to be analyzed is water-soluble and interference component gas is water-insoluble, the gas measurement apparatus removes the gas component to be analyzed from sample gas with the bubbling separator to obtain reference gas. Therefore, since interference component gas at the same concentration is present also in reference gas, influence by interference component gas can be canceled.

(Clause 3) In Clause 1 or 2, the bubbling separator uses as water to be used for bubbling, drainage water produced when the sample gas is cooled. In analysis of combustion gas, moisture in gas is condensed owing to natural cooling and hence water is supplied to the bubbling separator. Therefore, water does not have to externally be supplied to the bubbling separator.

(Clause 4) In Clause 1 or 2, the gas component to be analyzed further includes at least one of NO gas, CO gas, and $CO_2$ gas. The reference gas line further includes a reference gas switch arranged between the bubbling separator and the dehumidification apparatus, the reference gas switch selectively supplying gas that has passed through the bubbling separator and the atmosphere to the dehumidification apparatus.

(Clause 5) In Clause 4, light emitted from the light source to the sample cell is infrared light. The detection unit includes a first detector that detects a concentration of $SO_2$ gas and a second detector that detects a concentration of at least one of NO gas, CO gas, and $CO_2$ gas.

According to the configuration as above, a multiple-component gas measurement apparatus capable of accurately measuring water-soluble gas to be analyzed and further measuring water-insoluble gas to be analyzed can be obtained.

(Clause 6) In Clause 1 or 2, the gas component to be analyzed includes NO gas and $NO_2$ gas. The sample gas line includes a cooler that cools and dehumidifies the sample gas and a converter that converts $NO_2$ gas in gas that has passed through the cooler into NO gas. The gas measurement apparatus further includes a processing unit that measures a concentration of $NO_2$ gas based on an output from the detection unit when gas that has passed through the sample gas line is introduced into the sample cell and an output from the detection unit when gas that has passed through the bubbling separator is introduced into the sample cell.

(Clause 7) In Clause 6, light emitted from the light source to the sample cell is infrared light. The detection unit includes a first detector that detects a concentration of $SO_2$ gas and a second detector that detects a concentration of NO gas.

According to the configuration as above, a multiple-component gas measurement apparatus capable of secondarily measuring a concentration of $NO_2$ gas, detection of which separately from NO gas is normally difficult, can be obtained.

It should be understood that the embodiments disclosed herein are illustrative and non-restrictive in every respect. The scope of the present invention is defined by the terms of the claims rather than the description of the embodiments above and is intended to include any modifications within the scope and meaning equivalent to the terms of the claims.

REFERENCE SIGNS LIST 1 drain separator; 2, 12 cooler; 3 converter; 4, 14 filter; 5, 15 pump; 6, 16 needle valve; 7, 17 drain pot; 8 sample gas switch; 8M, 8R, 13 three-way valve; 9 sample cell; 9a, 59a gas inlet; 9b, 59b gas outlet; 10 light source; 11 bubbling separator; 18 sector; 18e sector rotation axis; 19 motor; 20, 22, 23, 24, 25 detector; 20A detection unit; 30 control device; 59 reference cell; 100, 100A, 200, 200A, 500 gas measurement apparatus; ML sample gas line; RL, RLA reference gas line

The invention claimed is:

1. A gas measurement apparatus that measures a gas component to be analyzed in sample gas, the gas measurement apparatus comprising:
   a sample gas supply line that supplies the sample gas;
   a sample gas line that has a first dehumidifier that dehumidifies the sample gas supplied from the sample gas supply line;
   a reference gas line that has a gas component remover that removes the gas component to be analyzed from the sample gas supplied from the sample gas supply line and a second dehumidifier that dehumidifies the sample gas after the gas component to be analyzed is removed by the gas component remover to generate reference gas;
   a sample cell;
   a sample gas switch that selectively supplies to the sample cell, gas that has passed through the reference gas line and gas that has passed through the sample gas line;
   a light source that irradiates the sample cell with light; and
   a detection unit that detects intensity of light that has passed through the sample cell after being emitted from the light source to the sample cell,
   wherein the gas component to be analyzed includes $SO_2$ gas,
   wherein the gas component remover is a bubbling separator that bubbles the sample gas with water to remove $SO_2$ gas from the sample gas,
   wherein the second dehumidifier is a dehumidification apparatus that dehumidifies gas that has passed through the bubbling separator, and
   wherein the bubbling separator uses as the water to be used for bubbling, drainage water produced when the sample gas is cooled.

2. A gas measurement apparatus that measures a gas component to be analyzed in sample gas, the gas measurement apparatus comprising:
   a sample gas supply line that supplies the sample gas;
   a sample gas line that has a first dehumidifier that dehumidifies the sample gas;
   a reference gas line that has a gas component remover that removes the gas component to be analyzed from the sample gas supplied from the sample gas supply line and a second dehumidifier that dehumidifies the sample gas after the gas component to be analyzed is removed by the gas component remover to generate reference gas;
   a sample cell into which gas that has passed through the sample gas line is introduced;
   a reference cell into which gas that has passed through the reference gas line is introduced;
   a light source that irradiates the sample cell and the reference cell with light; and
   a detection unit that detects intensity of light that has passed through the sample cell after being emitted from the light source to the sample cell and intensity of light that has passed through the reference cell after being emitted from the light source to the reference cell,
   wherein the gas component to be analyzed includes $SO_2$ gas,
   wherein the gas component remover is a bubbling separator that bubbles the sample gas with water to remove $SO_2$ gas from the sample gas, and
   wherein the second dehumidifier is a dehumidification apparatus that dehumidifies gas that has passed through the bubbling separator, and
   wherein the bubbling separator uses as the water to be used for bubbling, drainage water produced when the sample gas is cooled.

3. The gas measurement apparatus according to claim 1, wherein,
   the gas component to be analyzed further includes at least one of NO gas, CO gas, and $CO_2$ gas, and
   the reference gas line further includes a reference gas switch arranged between the bubbling separator and the dehumidification apparatus, the reference gas switch selectively supplying gas that has passed through the bubbling separator and the atmosphere to the dehumidification apparatus.

4. The gas measurement apparatus according to claim 3, wherein:

light emitted from the light source to the sample cell is infrared light, and the detection unit includes:

a first detector that detects a concentration of $SO_2$ gas, and a second detector that detects a concentration of at least one of NO gas, CO gas, and $CO_2$ gas.

5. The gas measurement apparatus according to claim 1, wherein:

the gas component to be analyzed includes NO gas and $NO_2$ gas, the first dehumidifier is a cooler that cools and dehumidifies the sample gas, the sample gas line further has a converter that converts $NO_2$ gas in gas that has passed through the cooler into NO gas, and the gas measurement apparatus further comprises a central processing unit that measures a concentration of $NO_2$ gas based on an output from the detection unit when gas that has passed through the sample gas line is introduced into the sample cell and an output from the detection unit when gas that has passed through the bubbling separator is introduced into the sample cell.

6. The gas measurement apparatus according to claim 5, wherein;

light emitted from the light source to the sample cell is infrared light, and the detection unit includes:

a first detector that detects a concentration of $SO_2$ gas, and a second detector that detects a concentration of NO gas.

7. The gas measurement apparatus according to claim 2, wherein:

the gas component to be analyzed further includes at least one of NO gas, CO gas, and $CO_2$ gas, and the reference gas line further includes a reference gas switch arranged between the bubbling separator and the dehumidification apparatus, the reference gas switch selectively supplying gas that has passed through the bubbling separator and the atmosphere to the dehumidification apparatus.

8. The gas measurement apparatus according to claim 7, Wherein, light emitted from the light source to the sample cell is infrared light, and the detection unit includes;

a first detector that detects a concentration of $SO_2$ gas, and a second detector that detects a concentration of at least one of NO gas, CO gas, and $CO_2$ gas.

9. The gas measurement apparatus according to claim 2, wherein:

the gas component to be analyzed includes NO gas and $NO_2$ gas, the first dehumidifier is a cooler that cools and dehumidifies the sample gas, the sample gas line further has a converter that converts $NO_2$ gas in gas that has passed through the cooler into NO gas, and the gas measurement apparatus further comprises a central processing unit that measures a concentration of $NO_2$ gas based on an output from the detection unit when gas that has passed through the sample gas line is introduced into the sample cell and an output from the detection unit when gas that has passed through the bubbling separator is introduced into the reference cell.

10. The gas measurement apparatus according to claim 9, wherein:

light emitted from the light source to the sample cell is infrared light, and the detection unit includes:

a first detector that detects a concentration of $SO_2$ gas, and a second detector that detects a concentration of NO gas.

* * * * *